(12) United States Patent
Arai

(10) Patent No.: US 11,224,397 B2
(45) Date of Patent: Jan. 18, 2022

(54) IMAGING CONTROL DEVICE, IMAGING CONTROL METHOD, AND IMAGING CONTROL PROGRAM

(71) Applicant: FUJIFILM Corporation, Tokyo (JP)

(72) Inventor: Takahisa Arai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/938,124

(22) Filed: Jul. 24, 2020

(65) Prior Publication Data
US 2021/0059632 A1 Mar. 4, 2021

(30) Foreign Application Priority Data
Aug. 27, 2019 (JP) .............................. JP2019-154277

(51) Int. Cl.
| | |
|---|---|
| *G06T 11/00* | (2006.01) |
| *A61B 6/00* | (2006.01) |
| *G06T 7/00* | (2017.01) |
| *A61B 6/02* | (2006.01) |
| *A61B 6/04* | (2006.01) |

(52) U.S. Cl.
CPC ................ *A61B 6/54* (2013.01); *A61B 6/025* (2013.01); *A61B 6/4452* (2013.01); *A61B 6/463* (2013.01); *G06T 11/005* (2013.01); *A61B 6/0414* (2013.01); *A61B 6/467* (2013.01); *A61B 6/502* (2013.01); *G06T 2210/41* (2013.01)

(58) Field of Classification Search
CPC ......... A61B 6/54; A61B 6/025; A61B 6/0414; A61B 6/4452; A61B 6/463; A61B 6/461; A61B 6/52; A61B 6/02; A61B 6/03; A61B 6/40; A61B 6/42; A61B 6/48; A61B 6/56; G06T 11/005; G06T 7/0012; G06T 7/0079; G06T 11/003; G06T 2207/10116; G06T 2207/30068
See application file for complete search history.

(56) References Cited

U.S. PATENT DOCUMENTS

2009/0123052 A1 5/2009 Ruth et al.
2018/0329609 A1* 11/2018 De Swarte .............. G06T 19/00

FOREIGN PATENT DOCUMENTS

JP 2014-128716 A 7/2014

* cited by examiner

*Primary Examiner* — Don K Wong
(74) *Attorney, Agent, or Firm* — Studebaker & Brackett PC

(57) ABSTRACT

A common region derivation unit derives a common region common to at least some of a plurality of projection images which correspond to a plurality of radiation source positions, respectively, and are acquired by directing an imaging apparatus to perform tomosynthesis imaging. In a case in which a width of the common region in a movement direction of a radiation source is equal to or greater than a predetermined threshold value, an image acquisition unit directs the imaging apparatus to perform the tomosynthesis imaging to acquire the plurality of projection images.

11 Claims, 11 Drawing Sheets

FIG. 7
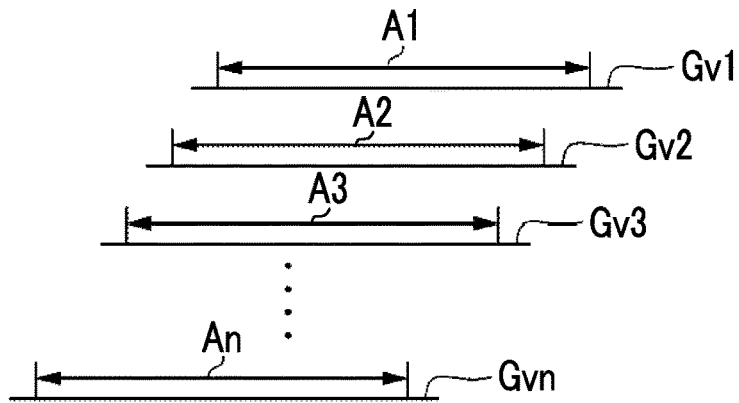
FIG. 8
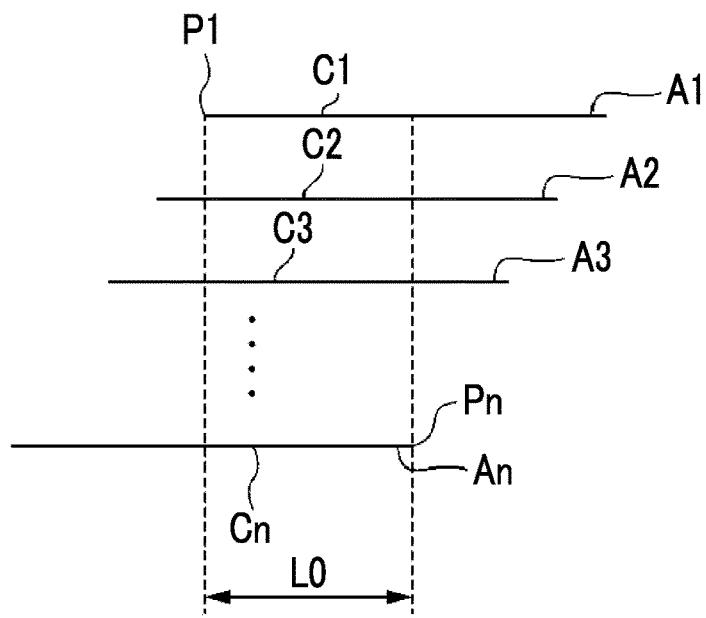
FIG. 9
| COMPRESSION THICKNESS (mm) | COMMON REGION WIDTH L0 (mm) |
|---|---|
| 10 | 232 |
| 20 | 228 |
| 149 | 181 |
TBL1

IMAGING CONTROL DEVICE, IMAGING CONTROL METHOD, AND IMAGING CONTROL PROGRAM

CROSS REFERENCE TO RELATED APPLICATIONS

The present application claims priority under 35 U.S.C. § 119 to Japanese Patent Application No. 2019-154277 filed on Aug. 27, 2019. The above application is hereby expressly incorporated by reference, in its entirety, into the present application.

BACKGROUND

Technical Field

The present disclosure relates to an imaging control device, an imaging control method, and an imaging control program.

Related Art

In recent years, image diagnosis using a radiography apparatus (called mammography) for capturing an image of the breast has attracted attention in order to promote early detection of breast cancer. Further, in the mammography, tomosynthesis imaging has been proposed which moves a radiation source, irradiates the breast with radiation from a plurality of radiation source positions to acquire a plurality of projection images, adds the plurality of acquired projection images to generate tomographic images in which desired tomographic planes have been highlighted. In the tomosynthesis imaging, the radiation source is moved in parallel to a radiation detector or is moved so as to draw a circular or elliptical arc according to the characteristics of an imaging apparatus and the required tomographic image and imaging is performed for the breast at a plurality of radiation source positions to acquire a plurality of projection images. Then, the projection images are reconstructed using a back projection method, such as a simple back projection method or a filtered back projection method, to generate tomographic images.

The tomographic images are generated in a plurality of tomographic planes of the breast, which makes it possible to separate structures that overlap each other in the depth direction in which the tomographic planes are arranged in the breast. Therefore, diagnosis is performed using the tomographic images generated by the tomosynthesis imaging to find a lesion that has been difficult to detect in a two-dimensional image (hereinafter, referred to as a simple two-dimensional image) acquired by simple imaging according to the related art.

In addition, a technique has been known which generates a pseudo two-dimensional image (hereinafter, referred to as a composite two-dimensional image) corresponding to the simple two-dimensional image, using a plurality of tomographic images having different distances (positions in a height direction) from a detection surface of a radiation detector to a radiation source, which have been acquired by tomosynthesis imaging (see JP2014-128716A).

However, in mammography, the breast is placed on an imaging table and imaging is performed in a state in which the breast is compressed by a compression plate. Therefore, the edge of the compression plate is included as a linear image in the image acquired by imaging. In a case in which the edge of the compression plate is bent upward to form a side wall, the side wall is included as a strip-shaped image (hereinafter, referred to as an edge image) in the image. Here, in the tomosynthesis imaging, the radiation source is moved to capture the image of the breast. Therefore, in particular, in a case in which the breast is irradiated with radiation in a direction inclined with respect to a perpendicular line to the detection surface of the radiation detector, the range in which the edge image of the compression plate is included in the projection image is extended. Therefore, in a case in which tomographic images are generated, the tomographic images are reconstructed using only regions obtained by excluding the edge image from the projection images such that artifacts caused by the edge image are not included in the tomographic images and the composite two-dimensional image.

In the tomosynthesis imaging, as described above, the radiation source is moved to capture the image of the breast. Therefore, the ranges of the breast images included in each of a plurality of projection images acquired by the tomosynthesis imaging are different from each other. In reconstruction, the quality of the generated tomographic image becomes higher as the number of projection images used becomes larger. Therefore, in the tomographic images and the composite two-dimensional image, a region common to all of the plurality of projection images has high image quality. However, as the number of projection images used for reconstruction becomes smaller, the quality of the tomographic images and the composite two-dimensional image becomes lower. As a result, in the tomographic images and the composite two-dimensional image, a high-quality region and a low-quality region are distributed in a strip shape in the movement direction of the radiation source.

Here, in mammography, it is important to find lesions, such as tumors and calcifications hidden by the mammary gland tissues and lymph node metastasis in terms of diagnosis. However, in a portion in which the quality of the tomographic images and the composite two-dimensional image deteriorates, it is difficult to find a lesion in image interpretation. As such, in a case in which it is difficult to find a lesion, the possibility of erroneous diagnosis due to the missing of a lesion increases.

SUMMARY OF THE INVENTION

The present disclosure has been made in view of the above-mentioned problems and an object of the present disclosure is to provide a technique that can reduce the possibility of erroneous diagnosis in a case in which image interpretation is performed using tomographic images and a composite two-dimensional image acquired by tomosynthesis imaging.

According to the present disclosure, there is provided an imaging control device that controls an imaging apparatus performing tomosynthesis imaging which relatively moves a radiation source with respect to a detection unit and irradiates an object with radiation at a plurality of radiation source positions caused by the movement of the radiation source. The imaging control device comprises: a common region derivation unit that derives a common region common to at least some of a plurality of projection images which correspond to the plurality of radiation source positions, respectively, and are acquired by directing the imaging apparatus to perform the tomosynthesis imaging; and an image acquisition unit that directs the imaging apparatus to perform the tomosynthesis imaging to acquire the plurality of projection images in a case in which a width of the common region in a movement direction of the radiation source is equal to or greater than a predetermined threshold value.

The "plurality of projection images which correspond to the plurality of radiation source positions, respectively, and are acquired by directing the imaging apparatus to perform the tomosynthesis imaging" means projection images acquired by performing the tomosynthesis imaging from now and does not mean projection images acquired by actually performing the tomosynthesis imaging.

The imaging control device according to the present disclosure may further comprise a warning unit that issues a warning indicating that the tomosynthesis imaging is not performed in a case in which the width of the common region in the movement direction of the radiation source is less than the predetermined threshold value.

In the imaging control device according to the present disclosure, the common region derivation unit may derive the common region on the basis of a geometric relationship between the object and the imaging apparatus.

In this case, the geometric relationship may include at least one of a thickness of the object, the plurality of radiation source positions, or a position of a detection surface of the detection unit.

The imaging control device according to the present disclosure may further comprise a reconstruction unit that reconstructs the plurality of projection images to generate a plurality of tomographic images.

The imaging control device according to the present disclosure may further comprise a combination unit that generates a composite two-dimensional image from the plurality of tomographic images.

In this case, the combination unit may weight and add values of corresponding pixels in the plurality of tomographic images to generate the composite two-dimensional image.

The imaging control device according to the present disclosure may further comprise a display control unit that displays at least some of the plurality of tomographic images on a display unit such that an effective image region corresponding to the common region is highlighted.

The imaging control device according to the present disclosure may further comprise a display control unit that displays at least some of the plurality of tomographic images or the composite two-dimensional image generated from the plurality of tomographic images on a display unit such that an effective image region corresponding to the common region is highlighted.

According to the present disclosure, there is provided an imaging control method that controls an imaging apparatus performing tomosynthesis imaging which relatively moves a radiation source with respect to a detection unit and irradiates an object with radiation at a plurality of radiation source positions caused by the movement of the radiation source. The imaging control method comprises: deriving a common region common to at least some of a plurality of projection images which correspond to the plurality of radiation source positions, respectively, and are acquired by directing the imaging apparatus to perform the tomosynthesis imaging; and directing the imaging apparatus to perform the tomosynthesis imaging to acquire the plurality of projection images in a case in which a width of the common region in a movement direction of the radiation source is equal to or greater than a predetermined threshold value.

In addition, a program that causes a computer to perform the imaging control method according to the present disclosure may be provided.

Another imaging control device according to the present disclosure comprises: a memory that stores commands for causing a computer to perform a process of controlling an imaging apparatus performing tomosynthesis imaging which relatively moves a radiation source with respect to a detection unit and irradiates an object with radiation at a plurality of radiation source positions caused by the movement of the radiation source; and a processor configured to execute the stored commands. The processor performs a process of deriving a common region common to at least some of a plurality of projection images which correspond to the plurality of radiation source positions, respectively, and are acquired by directing the imaging apparatus to perform the tomosynthesis imaging and a process of directing the imaging apparatus to perform the tomosynthesis imaging to acquire the plurality of projection images in a case in which a width of the common region in a movement direction of the radiation source is equal to or greater than a predetermined threshold value.

According to the present disclosure, it is possible to reduce the possibility of missing a lesion in tomographic images and a composite two-dimensional image acquired by tomosynthesis imaging.

BRIEF DESCRIPTION OF THE DRAWINGS

FIG. 7 is a diagram illustrating necessary regions in a plurality of projection regions.

FIG. 8 is a diagram illustrating the derivation of a common region.

FIG. 9 is a diagram illustrating a table defining the relationship between the compression thickness of the breast and the width of the common region.

DETAILED DESCRIPTION

Figure 1:
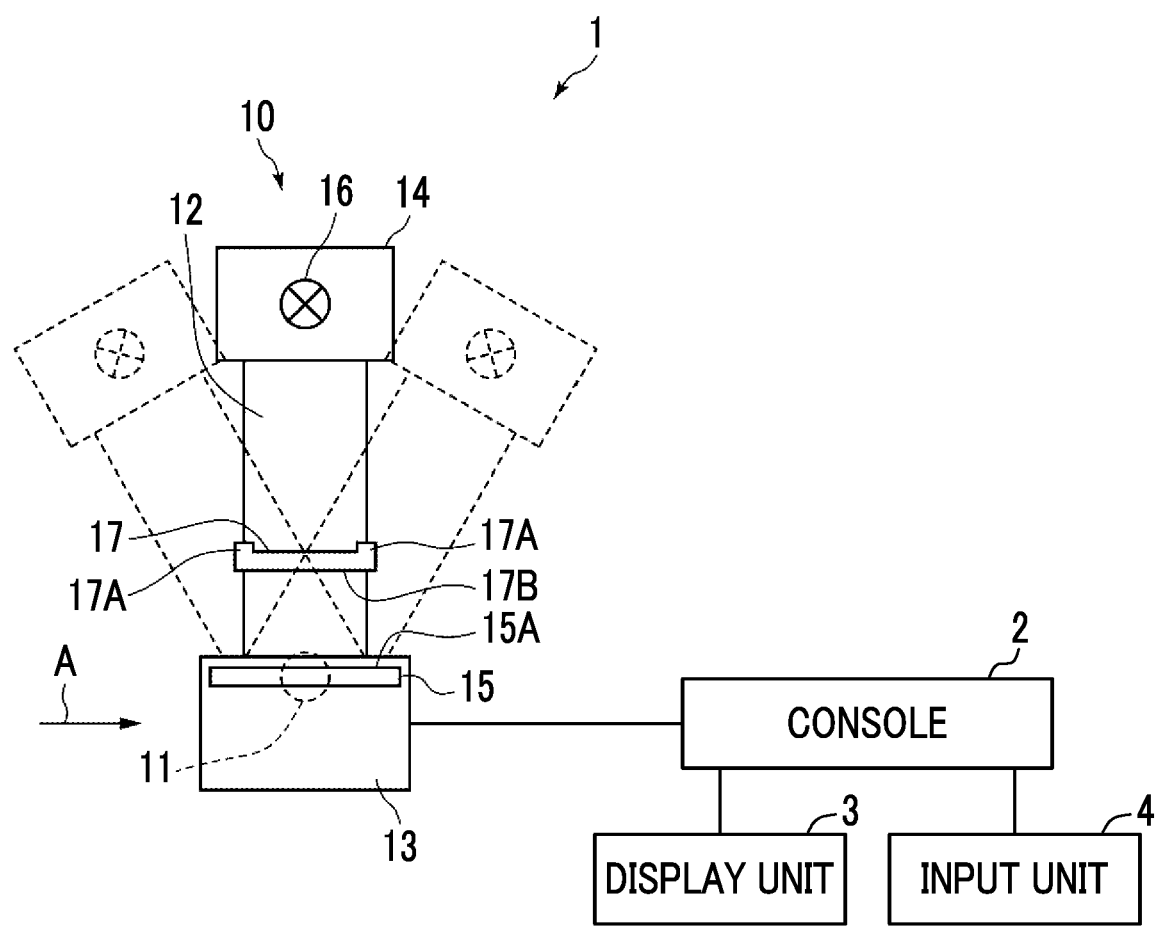
FIG. 1 is a diagram schematically illustrating a configuration of a radiography system to which an imaging control device according to an embodiment of the present disclosure is applied.
Figure 2:
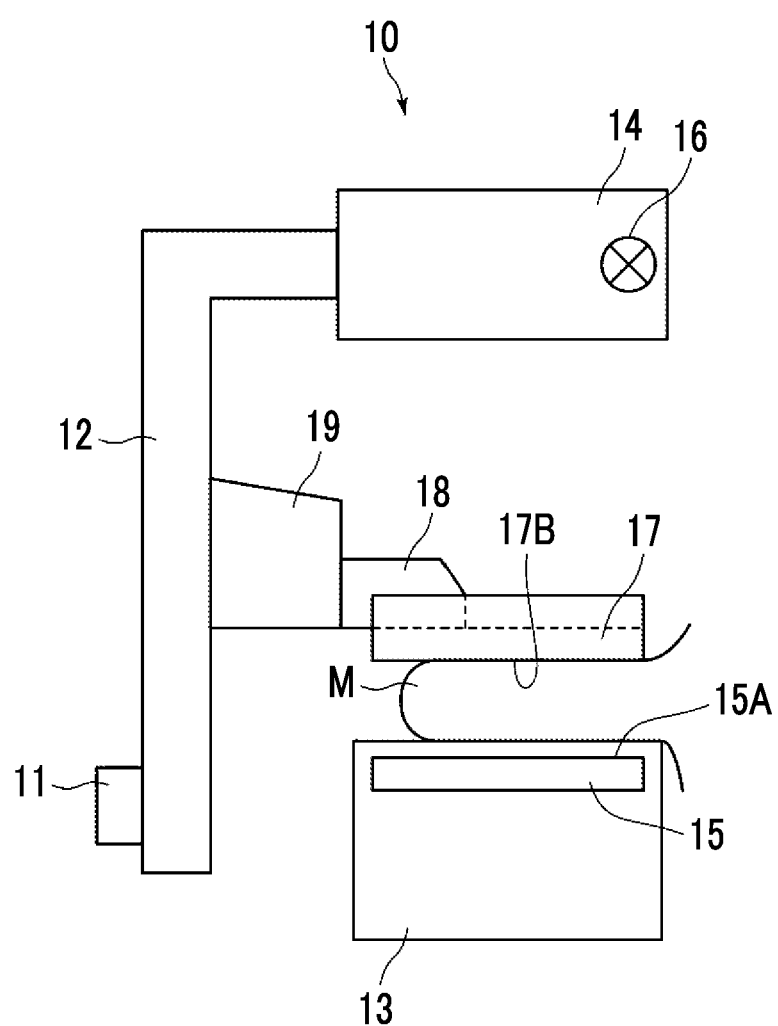
FIG. 2 is a diagram illustrating a mammography apparatus as viewed from a direction of an arrow A in FIG. 1.

Hereinafter, embodiments of the present disclosure will be described with reference to the drawings. FIG. 1 is a diagram schematically illustrating a configuration of a radiography system to which an imaging control device according to an embodiment of the present disclosure is applied and FIG. 2 is a diagram illustrating a mammography apparatus included in the radiography system as viewed from the direction of an arrow A in FIG. 1.

As illustrated in FIG. 1, a radiography system 1 according to this embodiment includes a console 2 and a mammography apparatus 10. The console 2 comprises a display unit 3 and an input unit 4.

The radiography system 1 according to this embodiment has a function of capturing the image of the breast using the mammography apparatus 10 on the basis of a command (imaging order) input from a radiology information system (RIS) through the console 2 in response to an operation of an operator, such as a doctor or a radiology technician, and acquiring a breast image which is a radiographic image of the breast. In this embodiment, the mammography apparatus 10 can perform both tomosynthesis imaging and simple imaging in various imaging directions to generate a tomographic image and a two-dimensional breast image of the breast. The two-dimensional breast image means a breast image acquired by the simple imaging. The mammography apparatus 10 corresponds to an imaging apparatus.

The mammography apparatus 10 comprises an arm portion 12 that is connected to a base (not illustrated) by a rotation shaft 11. An imaging table 13 is attached to one end of the arm portion 12 and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed and only the radiation emitting unit 14 can be rotated. The rotation of the arm portion 12 is controlled by the console 2.

A radiation detector 15, such as a flat panel detector, is provided in the imaging table 13. The radiation detector 15 has a radiation detection surface 15A. In addition, for example, a circuit substrate including a charge amplifier that converts a charge signal read from the radiation detector 15 into a voltage signal, a correlated double sampling circuit that samples the voltage signal output from the charge amplifier, and an analog-digital (AD) conversion unit that converts the voltage signal into a digital signal is provided in the imaging table 13.

The radiation detector 15 can repeatedly perform the recording and reading of a radiographic image and may be a so-called direct-type radiation detector that directly converts radiation into charge or a so-called indirect-type radiation detector that converts radiation into visible light once and converts the visible light into a charge signal. As a method for reading a radiographic image signal, it is desirable to use the following method: a so-called thin film transistor (TFT) reading method which turns on and off a TFT switch to read a radiographic image signal; or a so-called optical reading method which emits reading light to read a radiographic image signal. However, the reading method is not limited thereto and other methods may be used.

A radiation source 16 is accommodated in the radiation emitting unit 14. The radiation source 16 emits, for example, X-rays as radiation. The console 2 controls the timing when the radiation source 16 emits the radiation and the radiation generation conditions of the radiation source 16, that is, the selection of target and filter materials, a tube voltage, an irradiation time, and the like.

Further, the arm portion 12 is provided with a compression plate 17 that presses and compresses the breast M, a support portion 18 that supports the compression plate 17, and a movement mechanism 19 that moves the support portion 18 in the vertical direction in FIGS. 1 and 2. An interval between the compression plate 17 and the imaging table 13, that is, a compression thickness is input to the console 2. In addition, the compression plates 17 having a plurality of sizes and shapes corresponding to the types of imaging are prepared. Therefore, the compression plate 17 is attached to the support portion 18 so as to be interchangeable. Further, side walls 17A are formed at the left and right edges of the compression plate 17 in FIG. 1. The side walls 17A are formed in order to reduce the pain of a patient in a case in which the breast M compressed by a compression surface 17B of the compression plate 17 protrudes from the compression plate 17.

The display unit 3 is a display, such as a cathode ray tube (CRT) or a liquid crystal display, and displays messages required for operations in addition to a tomographic image and a composite two-dimensional image which will be described below. The display unit 3 may include a speaker that outputs sound.

The input unit 4 consists of a keyboard, a mouse, or a touch-panel-type input device and receives commands to operate the mammography apparatus 10 from the operator. In addition, the input unit 4 receives the input of various kinds of information required for tomosynthesis imaging, such as imaging conditions, and a command to correct information. In this embodiment, each unit of the mammography apparatus 10 is operated according to the information input by the operator through the input unit 4.

An imaging control program according to this embodiment is installed in the console 2. In this embodiment, the console 2 may be a workstation or a personal computer that is directly operated by the operator or a server computer that is connected to them through a network. The imaging control program is stored in a storage device of a server computer connected to a network or a network storage in a state where it can be accessed from the outside and is downloaded and installed in the computer as required. Alternatively, the imaging control program is recorded on a recording medium, such as a digital versatile disc (DVD) or a compact disc read only memory (CD-ROM), is distributed, and is installed in a computer from the recording medium.

Figure 3:
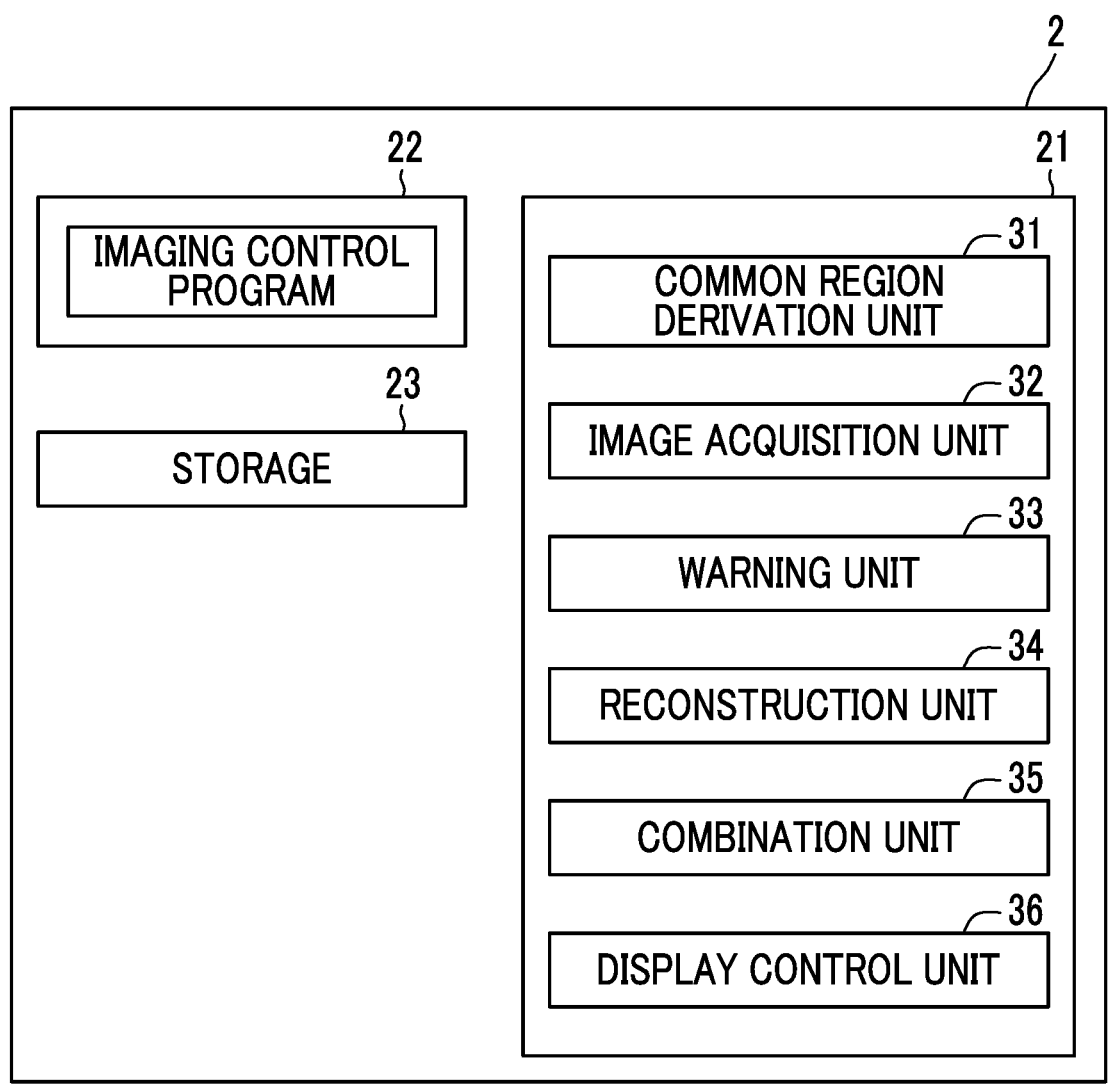
FIG. 3 is a diagram schematically illustrating a configuration of an imaging control device implemented by installing an imaging control program in a computer forming a console in this embodiment.

FIG. 3 is a diagram schematically illustrating a configuration of the imaging control device implemented by installing the imaging control program according to this embodiment in a computer forming the console 2. As illustrated in FIG. 3, the imaging control device comprises a central processing unit (CPU) 21, a memory 22, and a storage 23 as a standard computer configuration.

The storage 23 is a storage device, such as a hard disk drive or a solid state drive (SSD), and stores various kinds of information including the imaging control program and programs for driving each unit of the mammography apparatus 10. Further, for example, a projection image acquired by imaging, and tomographic images and a composite two-dimensional image generated as described below are stored in the storage 23.

The memory 22 temporarily stores, for example, the programs that are stored in the storage 23 in order to cause the CPU 21 to perform various processes. The imaging control program defines the following processes as the processes to be performed by the CPU 21: a common region derivation process that derives a common region common to at least some of a plurality of projection images which correspond to a plurality of radiation source positions, respectively, and are acquired by directing the mammography apparatus 10 to perform the tomosynthesis imaging; an image acquisition process that directs the mammography apparatus 10 to perform the tomosynthesis imaging to acquire a plurality of projection images of the breast M as an object in a case in which the width of the common region in the movement direction of the radiation source 16 is equal to or greater than a predetermined threshold value; a warning process that issues a warning indicating that the tomosynthesis imaging is not performed in a case in which the width of the common region in the movement direction of the radiation source 16 is less than the predetermined threshold value; a reconstruction process that reconstructs a plurality of projection images to generate a plurality of tomographic images in each of a plurality of tomographic planes of the breast M as the object in a case in which the plurality of projection images are acquired; a combination process that generates a composite two-dimensional image from the plurality of tomographic images; and a display control process that displays at least some of the plurality of tomographic images or the composite two-dimensional image on the display unit 3 such that a region corresponding to the common region is highlighted.

Then, the CPU 21 of the console 2 performs these processes according the imaging control program such that the CPU 21 functions as a common region derivation unit 31, an image acquisition unit 32, a warning unit 33, a reconstruction unit 34, a combination unit 35, and a display control unit 36.

In this embodiment, the common region derivation unit 31 derives the common region and imaging is performed for the breast M to acquire a plurality of projection images in a case in which the width of the derived common region in the movement direction of the radiation source 16 is less than the predetermined threshold value. First, the tomosynthesis imaging performed by the image acquisition unit 32 will be described.

Figure 4:
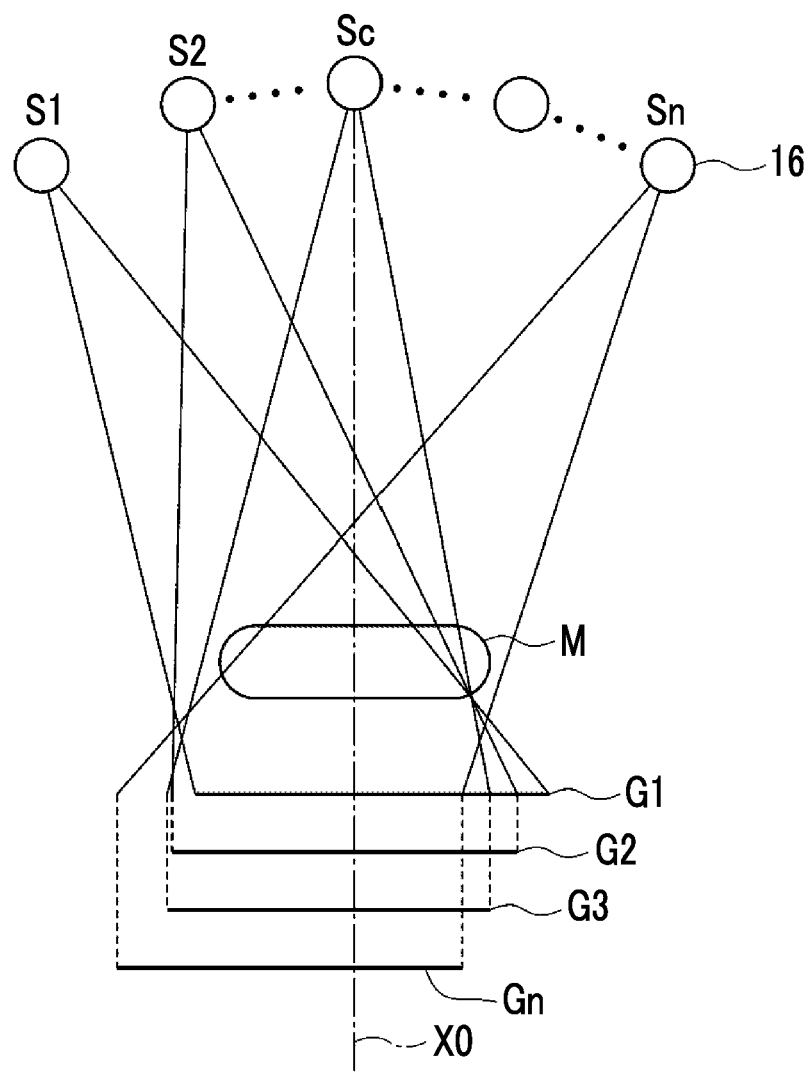
FIG. 4 is a diagram illustrating the acquisition of projection images.

The image acquisition unit 32 rotates the arm portion 12 around the rotation shaft 11 to move the radiation source 16, irradiates the breast M with radiation at a plurality of radiation source positions caused by the movement of the radiation source 16 according to imaging conditions for tomosynthesis imaging, detects the radiation transmitted through the breast M using the radiation detector 15, and acquires a plurality of projection images G1 (i=1 to n, where n is the number of radiation source positions and is, for example, 15) at a plurality of radiation source positions. FIG. 4 is a diagram illustrating the acquisition of the projection images Gi. As illustrated in FIG. 4, the radiation source 16 is moved to each of radiation source positions S1, S2, . . . , and Sn. The radiation source 16 is driven at each radiation source position to irradiate the breast M with radiation. The radiation detector 15 detects the radiation transmitted through the breast M to acquire projection images G1, G2, . . . , Gc, . . . , and Gn corresponding to the radiation source positions S1 to Sn, respectively. Here, the radiation source position Sc illustrated in FIG. 4 is a radiation source position where the optical axis XO of the radiation emitted from the radiation source 16 is orthogonal to the detection surface 15A of the radiation detector 15. Hereinafter, in some cases, the radiation source position Sc is referred to as a reference radiation source position Sc. At each of the radiation source positions S1 to Sn, the same dose of radiation is emitted to the breast M. The plurality of acquired projection images Gi are stored in the storage 23.

The common region derivation unit 31 derives a common region that is common to at least some of the plurality of projection images Gi acquired by directing the mammography apparatus 10 to perform the tomosynthesis imaging. In this embodiment, the common region derivation unit 31 derives the common region before the image of the breast M is captured. Therefore, the common region derivation unit 31 derives projection regions Gvi of the plurality of projection images Gi acquired by actually performing the tomosynthesis imaging. Here, the projection regions Gvi are matched with irradiation field regions on the detection surface 15A which correspond to each of the radiation source positions S1 to Sn. Therefore, the projection region Gvi can be derived on the basis of a geometric relationship among, for example, the plurality of radiation source positions S1 to Sn, the position of the detection surface 15A of the radiation detector 15, and the irradiation field of radiation emitted from the radiation source 16.

Figure 5:
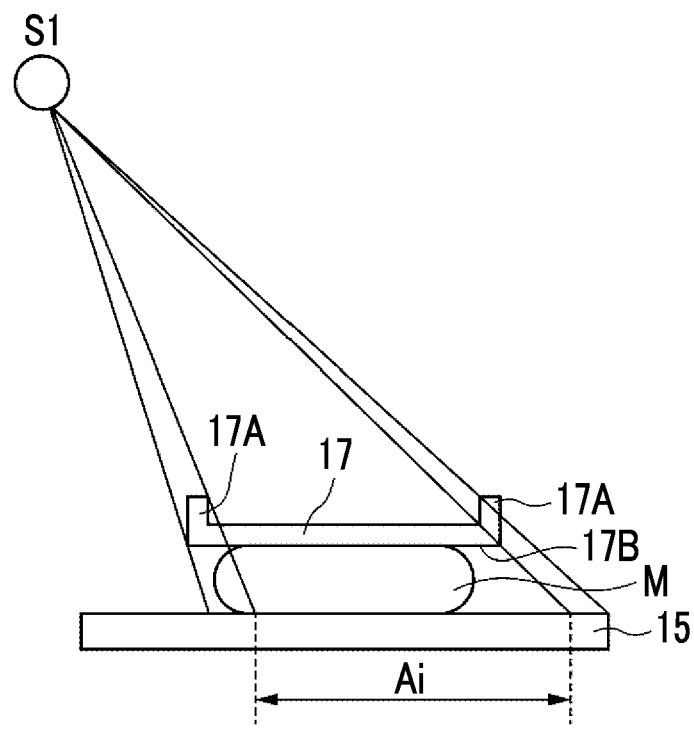
FIG. 5 is a diagram illustrating a geometric relationship among a radiation source, a compression plate, a breast, and a radiation detector.
Figure 6:
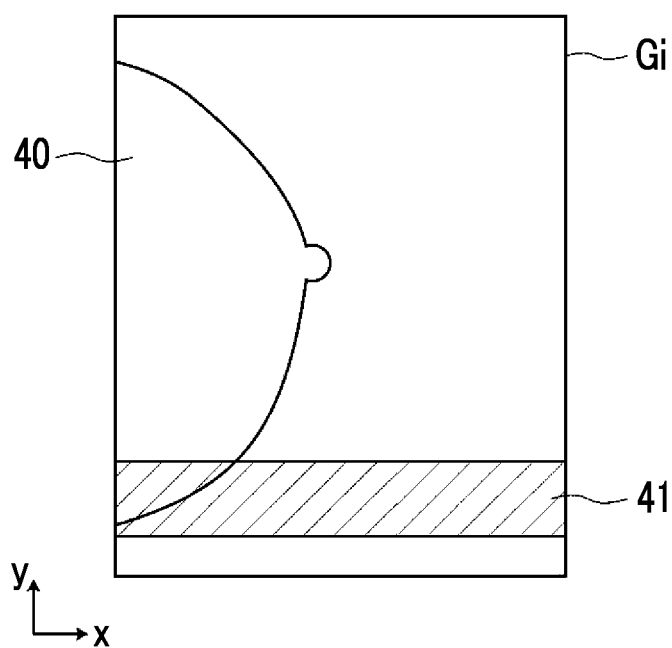
FIG. 6 is a diagram illustrating a projection image including an edge image.

Here, in this embodiment, the side wall 17A is formed at the edge of the compression plate 17. Therefore, particularly, in a case in which the position of the radiation source 16 is inclined with respect to a perpendicular line to the detection surface 15A of the radiation detector 15, the radiation transmitted through the side wall 17A is transmitted through the breast M and is detected by the radiation detector 15 as illustrated in FIG. 5. In this case, in the projection image Gi acquired by actually capturing the image of the breast M, as illustrated in FIG. 6, a strip-shaped image (hereinafter, referred to as an edge image 41) caused by the side wall 17A of the compression plate 17 is superimposed on the image of the breast M (hereinafter, referred to as a breast image 40) included in the projection image Gi. In the projection image Gi illustrated in FIG. 6, a coordinate system in which the movement direction of the radiation source 16 is the y direction is illustrated. As such, in a case in which the projection image Gi includes the strip-shaped edge image 41 corresponding to the side wall 17A, artifacts are included in the tomographic images generated by reconstructing the plurality of projection images Gi as described below.

Therefore, the common region derivation unit 31 extracts, as a necessary region Ai, a region corresponding to the radiation transmitted through only the compression surface 17B of the compression plate 17 in the plurality of projection regions Gvi. As illustrated in FIG. 5, the necessary region Ai corresponds to a region that is irradiated with the radiation transmitted through only the compression surface 17B of the compression plate 17 in the radiation detector 15. FIG. 7 is a diagram illustrating the necessary regions Ai in the plurality of projection regions Gvi. As illustrated in FIG. 7, the necessary region Ai has a width obtained by excluding both edges including the edge image in the movement direction of the radiation source 16 in the projection region Gvi.

Here, the size of the compression plate 17 and the height and thickness of the side wall 17A are known. The thickness of the breast M during imaging is equal to the height of the compression plate 17 and is known. Further, the plurality of radiation source positions S1 to Sn and the position of the detection surface 15A of the radiation detector 15 are known. Therefore, in this embodiment, the information of the size of the compression plate 17, the height of the side wall 17A, and the thickness of the compression plate 17 is stored in the storage 23. The common region derivation unit 31 reads the information of the size of the compression plate 17 used, the height of the side wall 17A, and the thickness of the compression plate 17 from the storage 23 and derives the positions of both edges of the necessary region Ai included in the projection region Gvi, using the geometric relationship among the thickness of the breast M, the radiation source positions S1 to Sn, and the position of the detection surface 15A of the radiation detector 15. Then, the common region derivation unit 31 extracts the necessary region Ai in the projection region Gvi on the basis of the derived positions of both edges.

Further, the common region derivation unit 31 derives a common region Ci that is common to at least some of the plurality of projection regions Gvi from the necessary region Ai. In this embodiment, the common region Ci that is common to all of the plurality of projection regions Gvi, that is, the plurality of necessary regions Ai is derived. FIG. 8 is a diagram illustrating the derivation of the common region Ci. The common region derivation unit 31 specifies necessary regions A1 and An of the projection regions Gvi and Gvn derived at the radiation source positions S1 and Sn at both ends on the detection surface 15A of the radiation detector 15 in order to derive the common region Ci. Then, the common region derivation unit 31 specifies edges P1 and Pn that are closest to the radiation source positions S1 and Sn in the necessary regions A1 and An, respectively. Here, as described above, the positions of both edges of the necessary regions A1 and An are known. Therefore, the common region derivation unit 31 extracts, as the common region Ci, a region that has, as both edges, the edges P1 and Pn of the necessary regions A1 and An among the plurality of necessary regions Ai. Then, the common region derivation unit 31 derives the width L0 of the common region Ci in the movement direction of the radiation source 16.

Here, the necessary region Ai and the common region Ci derived in the projection region Gvi are matched with the necessary region and the common region in the projection image Gi acquired by performing the tomosynthesis imaging. Therefore, in the following description, it is assumed that the necessary region and the common region in the projection image Gi are denoted by the same reference numerals as the necessary region Ai and the common region Ci derived in the projection region Gvi.

The width L0 of the common region Ci in the movement direction of the radiation source 16 which corresponds to the compression thickness of the breast M may be calculated in advance and may be stored as a table in the storage 23. FIG. 9 is a diagram illustrating a table defining the relationship between the compression thickness of the breast and the width L0 of the common region Ci. In FIG. 9, the unit of the compression thickness and the width L0 is mm Here, a table TBL1 illustrated in FIG. 9 shows values in a case in which, for example, the compression plate 17 has a size of 24 cm×30 cm and the deflection angle of the radiation source 16 during imaging is ±20 degrees. The common region derivation unit 31 derives the width L0 on the basis of the compression thickness of the breast M with reference to the table TBL1. In a case in which the compression thickness is a value other than the values illustrated in the table TBL1, the width L0 may be derived by an interpolation operation using the values in the table TBL1.

The image acquisition unit 32 compares the width L0 derived by the common region derivation unit 31 with a predetermined threshold value Th1. Then, in a case in which the width L0 is equal to or greater than the threshold value Th1, the tomosynthesis imaging is performed for the breast M as described above to acquire a plurality of projection images Gi. In a case in which the width L0 is less than the threshold value Th1, information indicating the fact is output to the warning unit 33.

Figure 10:
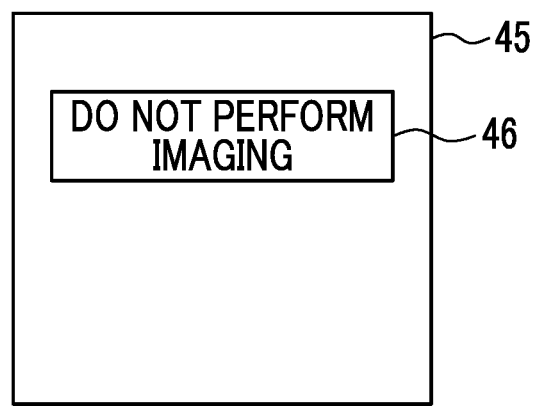
FIG. 10 is a diagram illustrating a warning screen.

In a case in which the width L0 of the common region Ci in the movement direction of the radiation source 16 is less than the threshold value Th1, the warning unit 33 issues a warning indicating that the tomosynthesis imaging is not performed. In this embodiment, the warning unit 33 displays a warning screen on the display unit 3. FIG. 10 is a diagram illustrating the warning screen. As illustrated in FIG. 10, a warning screen 45 includes a text 46 of "do not perform imaging". Then, the operator can recognize that the tomosynthesis imaging is not performed for the patient as an imaging target. In this embodiment, the warning unit 33 displays the warning screen on the display unit 3. However, the present disclosure is not limited thereto. The warning unit 33 may issue a warning using sound or may issue a warning using both sound and the warning screen.

Figure 11:
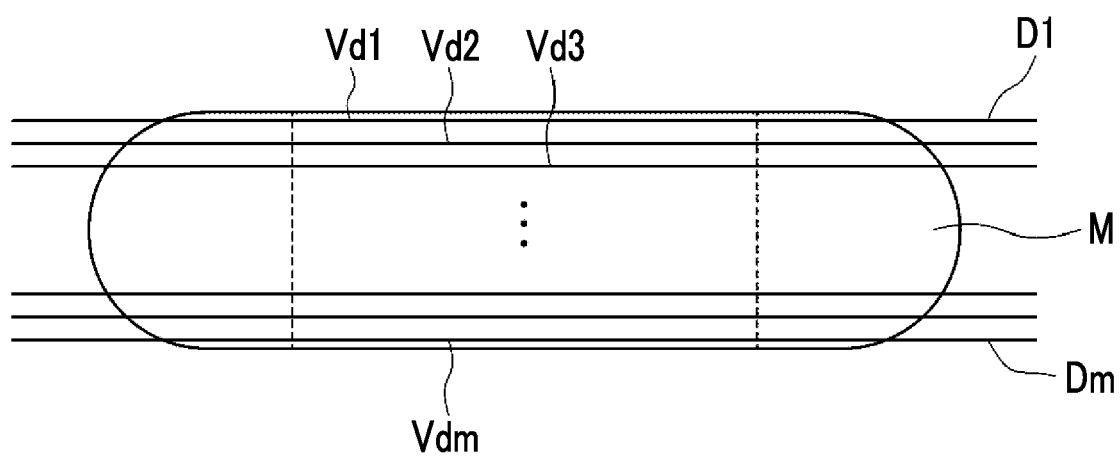
FIG. 11 is a diagram illustrating the generation of tomographic images.

The reconstruction unit 34 generates a tomographic image in which a desired tomographic plane of the breast M has been highlighted by reconstructing the necessary region Ai in the projection image Gi acquired by the tomosynthesis imaging. Specifically, the reconstruction unit 34 reconstructs the necessary regions Ai in the plurality of projection images Gi using a known back projection method, such as a simple back projection method or a filtered back projection method, to generate a plurality of tomographic images Dj (j=1 to m) in each of a plurality of tomographic planes of the breast M as illustrated in FIG. 11. In this case, a three-dimensional coordinate position in a three-dimensional space including the breast M is set, pixel values at corresponding pixel positions in the plurality of projection images Gi are reconstructed for the set three-dimensional coordinate position, and pixel values at the coordinate positions are calculated.

In the reconstruction, for the common region Ci in the necessary region Ai, the tomographic images Dj are reconstructed using all of information included in n projection images Gi. A region corresponding to the common region Ci in the tomographic image Dj is illustrated as an effective image region Vdj in FIG. 11. In the tomographic image Dj, as the distance from the effective image region Vdj becomes longer, the number of projection images Gi used for reconstruction, that is, the number of necessary regions Ai becomes smaller. Therefore, the amount of information is reduced. As a result, image quality deteriorates. Therefore, in the tomographic image Dj, the effective image region Vdj has the highest image quality in the movement direction of the radiation source 16 and the image quality gradually deteriorates toward the edge.

The combination unit 35 generates a composite two-dimensional image CG0 using the plurality of tomographic images Dj. The composite two-dimensional image CG0 is a pseudo two-dimensional image corresponding to a simple two-dimensional image that is captured by irradiating the breast M with radiation emitted at the reference radiation source position Sc. In this embodiment, the combination unit 35 generates the composite two-dimensional image CG0 using an addition method. The addition method is a method that weights and adds the values of the corresponding pixels in each of the plurality of tomographic images Dj along a viewing direction from the reference radiation source position Sc to the radiation detector 15, that is, the optical axis XO shown in FIG. 4 in a state in which the tomographic images Dj are stacked. A method for generating the composite two-dimensional image CG0 is not limited to the addition method and a known technique may be applied. In the addition method, a weight for each pixel during the weighting and addition is set to 1/m in a case in which m is the number of tomographic images Dj. In the composite two-dimensional image CG0, a region corresponding to the common region Ci, that is, a region corresponding to only the effective image region Vdj in the plurality of tomographic images Dj is referred to as an effective image region V0.

Figure 12:
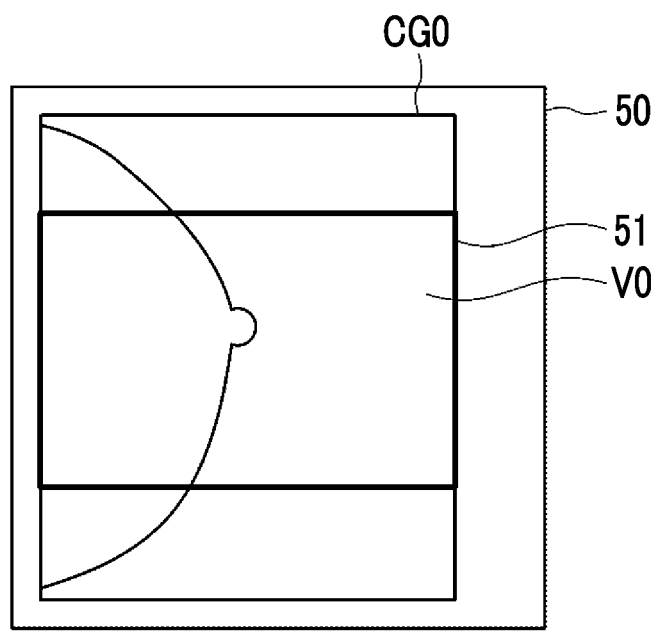
FIG. 12 is a diagram illustrating a composite two-dimensional image display screen.

The display control unit 36 displays at least some of the tomographic images Dj or the composite two-dimensional image CG0 on the display unit 3 in response to a command from the input unit 4. In this case, the tomographic images Dj or the composite two-dimensional image CG0 is displayed on the display unit 3 such that the effective image region Vdj in the tomographic image Dj and the effective image region V0 in the composite two-dimensional image CG0 are highlighted. FIG. 12 is a diagram illustrating a display screen for the composite two-dimensional image CG0. As illustrated in FIG. 12, the composite two-dimensional image CG0 is displayed on a display screen 50. A frame 51 is added to the effective image region V0 in the composite two-dimensional image CG0 to highlight the effective image region V0.

Figure 13:
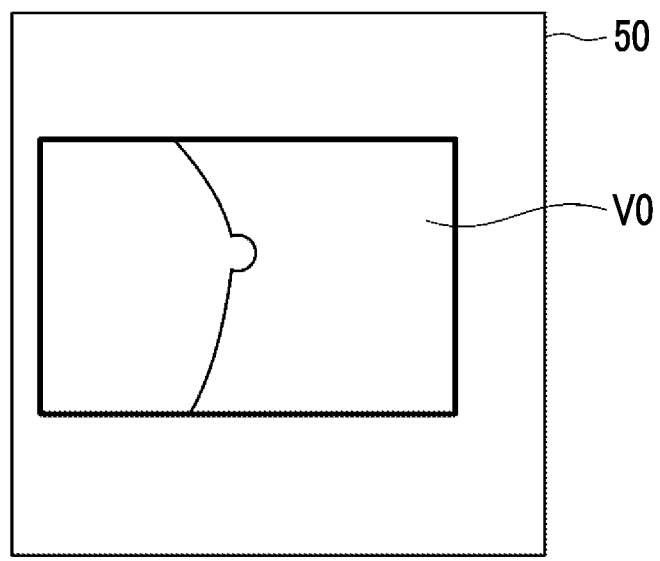
FIG. 13 is a diagram illustrating a composite two-dimensional image display screen.
Figure 14:
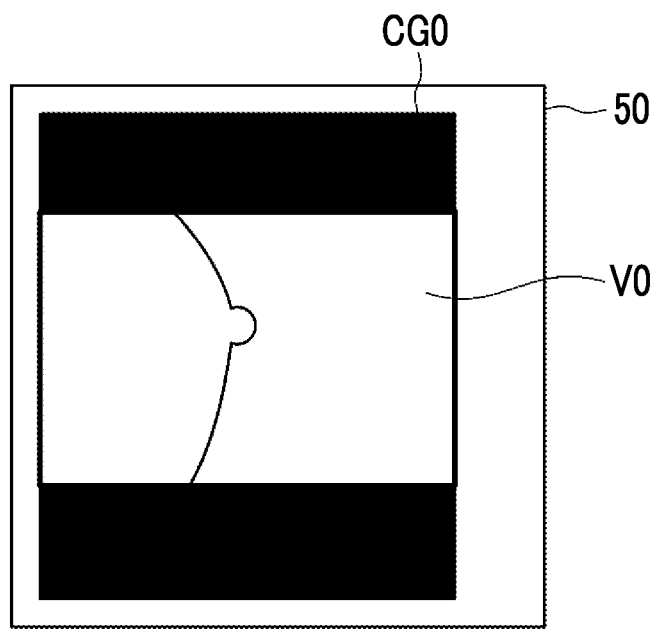
FIG. 14 is a diagram illustrating a composite two-dimensional image display screen.
Figure 15:
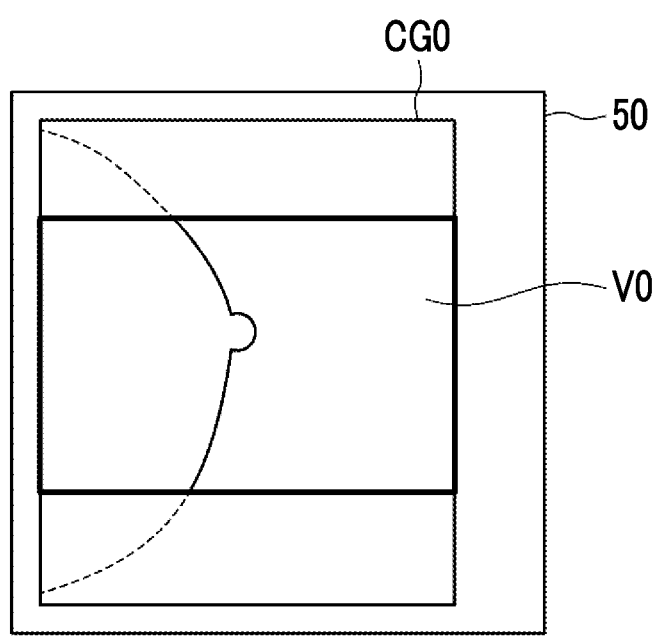
FIG. 15 is a diagram illustrating a composite two-dimensional image display screen.

As illustrated in FIG. 13, the display control unit 36 may trim only the effective image region V0 in the composite two-dimensional image CG0 to highlight the effective image region V0. Further, as illustrated in FIG. 14, a region other than the effective image region V0 in the composite two-dimensional image CG0 may be blacked out to highlight the effective image region V0. In addition, as illustrated in FIG. 15, the density of a region other than the effective image region V0 in the composite two-dimensional image CG0 may be reduced to highlight the effective image region V0. In FIG. 15, the contour of the breast included in the composite two-dimensional image CG0 is represented by a dashed line to indicate that the density is reduced.

In contrast, in a case in which the tomographic images Dj are displayed, the effective image region Vdj of each tomographic image Dj may be displayed so as to be highlighted as in the case in which the composite two-dimensional image CG0 is displayed. The tomographic images Dj to be displayed may be all of the tomographic images or only some of the tomographic images.

Figure 16:
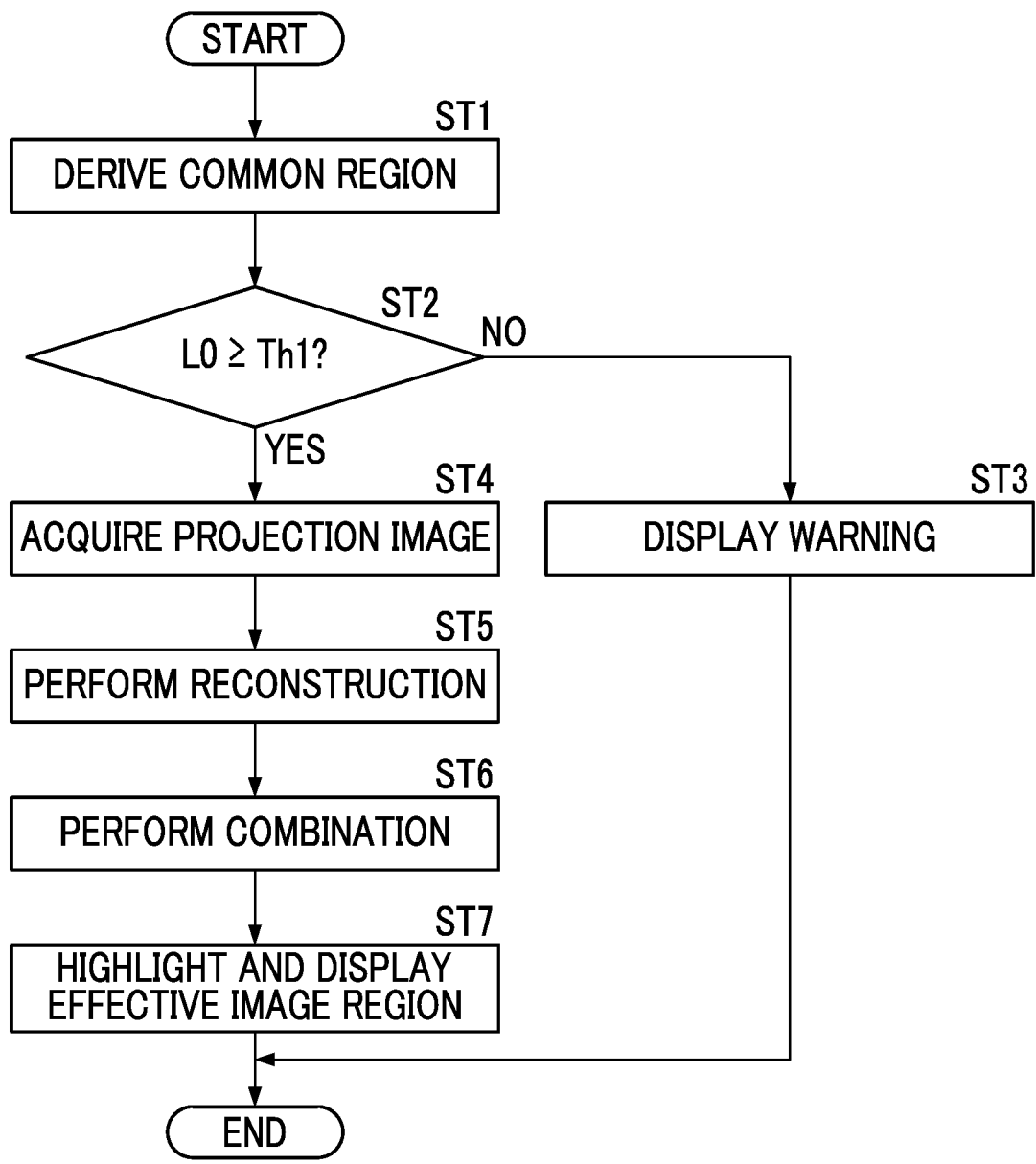
FIG. 16 is a flowchart illustrating a process performed in this embodiment.

Next, a process performed in this embodiment will be described. FIG. 16 is a flowchart illustrating a process performed in this embodiment. In a case in which the input unit 4 receives a process start command from the operator, the common region derivation unit 31 derives the common region Ci which is common to at least some of a plurality of projection images which correspond to a plurality of radiation source positions, respectively, and are acquired by directing the mammography apparatus 10 to perform the tomosynthesis imaging (Step ST1). Then, the common region derivation unit 31 determines whether the width L0 of the common region Ci in the movement direction of the radiation source 16 is equal to or greater than the predetermined threshold value Th1 (Step ST2). In a case in which the determination result in Step ST2 is "No", the warning unit 33 displays the warning screen on the display unit 3 (warning display; Step ST3). Then, the process ends.

In a case in which the determination result in Step ST2 is "Yes", the image acquisition unit 32 directs the mammography apparatus 10 to perform the tomosynthesis imaging to acquire a plurality of projection images Gi (Step ST4). Then, the reconstruction unit 34 reconstructs the plurality of projection images Gi to generate a plurality of tomographic images Dj in a plurality of tomographic planes of the breast M (Step ST5). The combination unit 35 combines the plurality of tomographic images Dj to generate the composite two-dimensional image CG0 (Step ST6). Then, the display control unit 36 displays at least some of the plurality of tomographic images Dj or the composite two-dimensional image CG0 on the display unit 3 such that the effective image regions Vdj and V0 are highlighted (effective image region highlight display; Step ST7). Then, the process ends.

As described above, in this embodiment, the common region Ci which is common to at least some of the plurality of projection images Gi which correspond to the plurality of radiation source positions S1 to Sn, respectively, and are acquired by directing the mammography apparatus 10 to perform the tomosynthesis imaging is derived before the tomosynthesis imaging. In a case in which the width L0 of the common region Ci in the movement direction of the radiation source 16 is equal to or greater than the predetermined threshold value Th1, the mammography apparatus 10 performs the tomosynthesis imaging.

Here, the tomographic images Dj generated from the projection images Gi and the composite two-dimensional image CG0 have higher quality as the number of common regions in the projection images Gi becomes larger. According to this embodiment, in a case in which the width L0 of the common region Ci in the movement direction of the radiation source 16 is less than the threshold value Th1, the tomosynthesis imaging is not performed. Therefore, an image in which the possibility of missing a lesion is high is not acquired. Therefore, according to this embodiment, it is possible to reduce the possibility of missing a lesion in the tomographic images Dj and the composite two-dimensional image CG0 acquired by the tomosynthesis imaging.

Further, in this embodiment, in a case in which at least some of the plurality of tomographic images Dj or the composite two-dimensional image CG0 generated from the plurality of tomographic images is displayed on the display unit 3, the effective image regions Vdj and V0 corresponding to the common region Ci are displayed so as to be highlighted. Here, the tomographic images Dj and the composite two-dimensional image CG0 have higher quality as the number of common regions in the projection images Gi becomes larger. Therefore, since the effective image regions Vdj and V0 corresponding to the common region Ci are displayed so as to be highlighted in the tomographic images Dj and the composite two-dimensional image CG0, the operator can more carefully interpret regions other than the highlighted effective image regions. Therefore, according to this embodiment, it is possible to reduce the possibility of missing a lesion in the tomographic images Dj and the composite two-dimensional image CG0 acquired by the tomosynthesis imaging.

Figure 17:
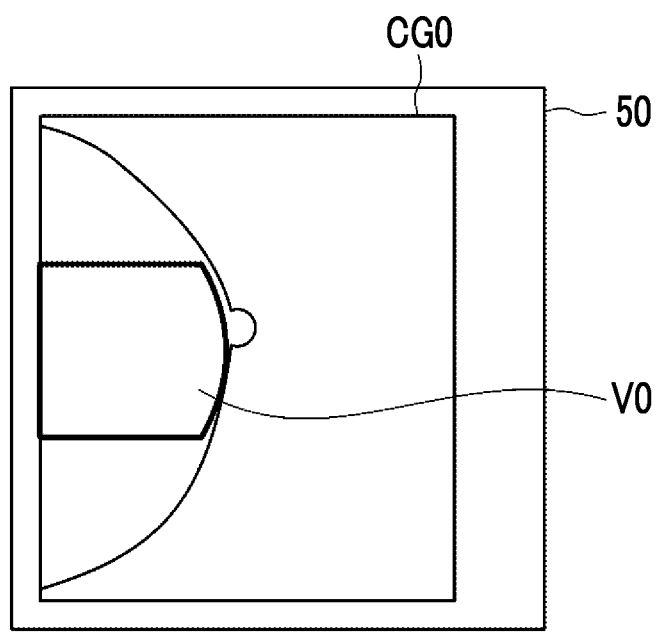
FIG. 17 is a diagram illustrating another example of the composite two-dimensional image display screen.

In the above-described embodiment, radiation is emitted from the radiation source 16 such that the optical axis XO passes in the vicinity of the chest wall of the breast M. Therefore, the positions of the nipples are different in the projection images G1 and Gn acquired at the radiation source positions S1 and Sn at both ends and the projection image Gc acquired at the reference radiation source position Sc. Therefore, the common region Ci may be derived considering the position of the nipple of the breast M included in the projection images Gi. In this case, in the effective image region V0 based on the derived common region Ci, a portion close to the nipple has a convex shape as illustrated in FIG. 17.

Further, in the above-described embodiment, in a case in which the tomographic images Dj or the composite two-dimensional image CG0 is displayed, the effective image regions Vdj and V0 are displayed so as to be highlighted. However, the tomographic images Dj or the composite two-dimensional image CG0 may be displayed such that the effective image regions Vdj and V0 are not highlighted.

In addition, in the above-described embodiment, the addition method is applied as the method for generating the composite two-dimensional image in the combination unit 35. However, other known techniques may be applied as described above. For example, a so-called minimum path method using the minimum value of the corresponding pixel of each tomographic image may be applied.

Further, the radiation in the above-described embodiment is not particularly limited. For example, $\alpha$-rays or $\gamma$-rays can be applied in addition to the X-rays.

In the above-described embodiment, the necessary region Ai is extracted from the projection region Gvi. However, the present disclosure is not limited thereto. The common region Ci may be derived without extracting the necessary region Ai.

Further, in the above-described embodiment, for example, the following various processors can be used as the hardware structure of processing units performing various processes, such as the common region derivation unit 31, the image acquisition unit 32, the warning unit 33, the reconstruction unit 34, the combination unit 35, and the display control unit 36. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. An imaging control device that controls an imaging apparatus performing tomosynthesis imaging which relatively moves a radiation source with respect to a radiation detector and irradiates an object with radiation at a plurality of radiation source positions caused by the movement of the radiation source, the imaging control device comprising at least one processor, wherein the processor is configured to:
   derive a common region common to at least some of a plurality of projection images which correspond to the plurality of radiation source positions, respectively, and are acquired by directing the imaging apparatus to perform the tomosynthesis imaging; and
   direct the imaging apparatus to perform the tomosynthesis imaging to acquire the plurality of projection images in a case in which a width of the common region in a movement direction of the radiation source is equal to or greater than a predetermined threshold value.

2. The imaging control device according to claim 1, wherein the processor is configured to issue a warning indicating that the tomosynthesis imaging is not performed in a case in which the width of the common region in the movement direction of the radiation source is less than the predetermined threshold value.

3. The imaging control device according to claim 1, wherein the processor is configured to derive the common region on the basis of a geometric relationship between the object and the imaging apparatus.

4. The imaging control device according to claim 3, wherein the geometric relationship includes at least one of a thickness of the object, the plurality of radiation source positions, or a position of a detection surface of the radiation detector.

5. The imaging control device according to claim 1, wherein the processor is configured to reconstruct the plurality of projection images to generate a plurality of tomographic images.

6. The imaging control device according to claim 5, wherein the processor is configured to generate a composite two-dimensional image from the plurality of tomographic images.

7. The imaging control device according to claim 6, wherein the processor is configured to weight and add values of corresponding pixels in the plurality of tomographic images to generate the composite two-dimensional image.

8. The imaging control device according to claim 5, wherein the processor is configured to display at least some of the plurality of tomographic images on a display such that an effective image region corresponding to the common region is highlighted.

9. The imaging control device according to claim 5, wherein the processor is configured to display at least some of the plurality of tomographic images or the composite two-dimensional image generated from the plurality of tomographic images on a display such that an effective image region corresponding to the common region is highlighted.

10. An imaging control method that controls an imaging apparatus performing tomosynthesis imaging which relatively moves a radiation source with respect to a radiation detector and irradiates an object with radiation at a plurality of radiation source positions caused by the movement of the radiation source, the imaging control method comprising:
   deriving a common region common to at least some of a plurality of projection images which correspond to the plurality of radiation source positions, respectively, and are acquired by directing the imaging apparatus to perform the tomosynthesis imaging; and
   directing the imaging apparatus to perform the tomosynthesis imaging to acquire the plurality of projection images in a case in which a width of the common region in a movement direction of the radiation source is equal to or greater than a predetermined threshold value.

11. A non-transitory computer-readable storage medium that stores an imaging control program that causes a computer to perform an imaging control method which controls an imaging apparatus performing tomosynthesis imaging which relatively moves a radiation source with respect to a radiation detector and irradiates an object with radiation at a plurality of radiation source positions caused by the movement of the radiation source, the imaging control program causing the computer to perform:

deriving a common region common to at least some of a plurality of projection images which correspond to the plurality of radiation source positions, respectively, and are acquired by directing the imaging apparatus to perform the tomosynthesis imaging; and directing the imaging apparatus to perform the tomosynthesis imaging to acquire the plurality of projection images in a case in which a width of the common region in a movement direction of the radiation source is equal to or greater than a predetermined threshold value.

* * * * *